United States Patent [19]

Grollier et al.

[11] Patent Number: 5,063,051
[45] Date of Patent: Nov. 5, 1991

[54] COSMETIC HAIR-CARE COMPOSITION BASED ON POLYORGANOSILOXANES CONTAINING A HYDROXYALKYL FUNCTIONAL GROUP

[75] Inventors: Jean F. Grollier, Paris; Claude Dubief, Le Chesnay; Christine Dupuis, Paris, all of France

[73] Assignee: L'Oreal, Paris, France

[21] Appl. No.: 376,742

[22] Filed: Jul. 7, 1989

[30] Foreign Application Priority Data

Jul. 12, 1988 [LU] Luxembourg ........................ 87273

[51] Int. Cl.$^5$ .......................... A61K 7/06; A61K 7/08
[52] U.S. Cl. ......................................... 424/70; 424/47; 424/78; 424/71; 514/772
[58] Field of Search ................ 424/47, 70, 71, 78; 514/772

[56] References Cited

U.S. PATENT DOCUMENTS

| | | | |
|---|---|---|---|
| 2,970,150 | 1/1961 | Bailey | 525/479 X |
| 3,159,601 | 12/1964 | Ashby | 525/478 X |
| 3,195,662 | 12/1964 | Ashby | 525/479 X |
| 3,436,366 | 4/1969 | Modic | 525/477 X |
| 3,715,334 | 2/1973 | Karstedt | 525/475 X |
| 3,775,452 | 11/1973 | Karstedt | 528/18 X |
| 3,814,730 | 6/1974 | Karstedt | 525/475 X |
| 4,160,775 | 7/1979 | Schilling, Jr. | 556/440 X |
| 4,342,742 | 8/1982 | Sebag et al. | 424/70 X |
| 4,839,166 | 6/1989 | Grollier et al. | 424/71 X |

Primary Examiner—Thurman K. Page
Assistant Examiner—Susan S. Rucker
Attorney, Agent, or Firm—Marshall, O'Toole, Gerstein, Murray & Bicknell

[57] ABSTRACT

Cosmetic hair-care composition containing a polyorganosiloxane containing a hydroalkyl functional group of formula:

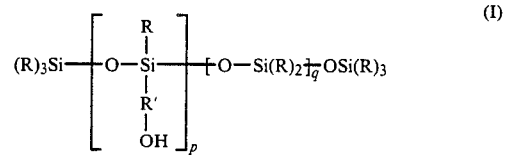

in which the radicals R denote methyl or phenyl, at least 60 mol % of the radicals R denoting methyl, the radical R' is a $C_2$–$C_{18}$ divalent alkylene hydrocarbon radical, p is an integer between 1 and 30 inclusive, q is an integer between 1 and 120 inclusive, this composition containing no anionic surface-active agents in sufficient proportions to impart foaming properties to the composition.

14 Claims, No Drawings

COSMETIC HAIR-CARE COMPOSITION BASED ON POLYORGANOSILOXANES CONTAINING A HYDROXYALKYL FUNCTIONAL GROUP

The present invention relates to a cosmetic haircare composition based on polyorganosiloxanes containing a hydroxyalkyl functional group and to processes for treating hair with the said composition.

Certain polyorganosiloxanes are well known in the field of cosmetic hair care and have been employed as hair conditioning agents, sought after especially to obtain gleaming hair. These are essentially phenylmethylpolysiloxanes which are present in cosmetic compositions which are generally applied to hair without this application being followed by a rinsing.

However, the disadvantage of these compounds is that they make hair heavy. From the viewpoint of aesthetics, what is looked for in hair styles is properties of sheen combined with a light and full appearance.

The applicants have surprisingly found that the use of polyorganosiloxanes containing a hydroxyalkyl functional group imparted a gleaming appearance to the hair and made it possible to obtain light and full hair, which is sought after in cosmetics.

"Cosmetic treatment" is the name given to a treatment intended to obtain one or more of the results indicated above in respect of hair.

A subject of the invention consists of the cosmetic compositions intended for the treatment of hair making use of polyorganosiloxanes containing a hydroxyalkyl functional group and containing no anionic surfaceactive agents in proportions imparting foaming properties to the compositions.

Another subject of the invention is a process for cosmetic treatment of hair making use of these compositions as styling products.

Other subjects of the invention will become apparent on reading the description and the examples which follow.

The main subject of the present invention is therefore a cosmetic hair-care composition containing, in a cosmetically acceptable medium, at least one polyorganosiloxane containing a hydroxyalkyl functional group corresponding to the following formula (I):

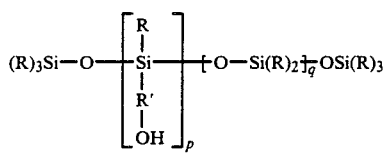

in which the radicals R, which are identical or different, are chosen from methyl and phenyl radicals, at least 60 mol % of the radicals R being methyl radicals, the radical R' is a linear or branched divalent alkylene hydrocarbon chain containing from 2 to 18 carbon atoms;

p is an integer between 1 and 30 inclusive, preferably between 1 and 20 inclusive;

q is an integer between 1 and 120 inclusive, this composition containing no anionic surface-active agents in proportions imparting foaming properties to the composition.

The copolymer according to the invention may be an alternating or random copolymer.

Among the particularly preferred compounds employed in accordance with the invention there may be mentioned the compounds of formula (I) in which:

R' denotes a linear or branched divalent alkylene hydrocarbon chain containing from 2 to 6 carbon atoms and, more particularly, a trimethylene chain:
—(CH$_2$—)$_3$ or a 2-methyltrimethylene chain:

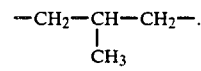

Among the products of formula (I) it is preferred to employ products whose number-average molecular mass is between 600 and 10,000.

Products of formula (I) which are more particularly preferred are represented by products of numberaverage molecular mass of between 1000 and 10,000, in which case p is between 1 and 5 and q is between 10 and 100.

The products of formula (I) are known in the industry and can be prepared according to known processes of the prior art, such as those described in French Patent No. 2589476.

To prepare the products of formula (I) it is possible, for example, to employ as a starting organopolysiloxane the copolymer of formula (II):

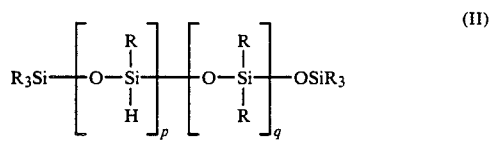

in which R, p and q have the meaning given above.

These products are well known in the silicones industry and are generally available commercially. They are described, for example, in U.S. Pat. No. 3,436,366.

The products of formula (II) are reacted with an alcohol containing alkene unsaturation of formula (III): R"OH, in which R" is a linear or branched alkenylene radical containing from 2 to 18 carbon atoms. Among these alcohols, those more particularly employed are allyl alcohol and methallyl alcohol.

Known hydrosilylation catalysts may be employed as a hydrosilylation catalyst to react the unsaturated alcohols of formula (III) with the hydropolysiloxane of formula (II), especially the platinum complexes described in U.S. Pat. Nos. 3,715,334, 3,775,452 and 3,814,730, and platinum olefin complexes described in U.S. Pat. Nos. 3,159,601 and 3,159,662.

Procedures for preparing products of formula (I) are described in detail in U.S. Pat. Nos. 2,970,150 and 4,160,775.

The cosmetic compositions for the treatment and the care of hair in accordance with the invention contain, in a cosmetically acceptable medium, a polyorganosiloxane containing a hydroxyalkyl functional group of formula (I) in concentrations of between 0.5 and 50%, and preferably between 1 and 30%, relative to the total weight of the composition.

These compositions can be in the form of thickened or unthickened aqueous, alcoholic or hydroalcoholic or organic solvent-based lotions, in the form of gels or packaged as an aerosol or in a pump bottle to form sprays.

In addition to the polyorganosiloxane of formula (I) they may contain adjuvants which are usually employed in cosmetics, such as perfumes, colorants, preserving agents, thickeners, nonionic, cationic or amphoteric surface-active agents or a mixture thereof, sunscreens and active substances.

This composition contains no anionic surface-active agent in proportions imparting foaming properties to the composition.

This proportion is lower than 5% and preferably lower than 3% by weight relative to the total weight of the composition, the latter preferably containing no anionic surface-active agent.

The cosmetic compositions intended for treating hair, in accordance with the invention, are preferably employed in applications which are not followed by a rinsing. They may be employed in particular as unrinsed styling products, such as in hair-setting or blow-drying gels or lotion or in lacquers.

When the unrinsed cosmetic compositions according to the invention are in the form of lotions, the solvent medium may be chosen from lower $C_2-C_4$ alcohols and preferably from ethyl alcohol or from volatile silicones such as the cyclic silicones described in the CTFA dictionary under the names Hexamethylsiloxanes and Cyclomethicones or mixtures thereof, or else from hydrocarbons such as, preferably, butane and chlorofluorohydrocarbons, preferably chosen from trichlorofluoromethane and chlorodifluoromethane.

The solvents may be present in these unrinsed compositions in concentrations of between 50 and 99.5% and preferably between 70 and 98% relative to the total weight of the composition.

When the compositions according to the invention are in the form of thickened lotions or of gels, the solvent medium may be water or a water/alcohol mixture, the alcohol being a lower $C_2-C_4$ alcohol and preferably ethyl alcohol, present in proportions of between 0 and 50% relative to the total weight of the composition. The pH of these compositions is generally close to neutrality and is adjusted with conventional alkalifying or acidifying agents which are usually employed in the cosmetic hair-care field.

Rinsed compositions may be in the form of a lotion or gel to be applied after shampooing, dyeing or bleaching hair, or permanent-waving.

When the compositions are thickened or are in the form of gels, they contain one or more thickeners which may be chosen preferably from cellulose derivatives such as methyl cellulose, hydroxymethyl cellulose, hydroxyethyl cellulose, hydroxypropyl cellulose, hydroxypropyl methyl cellulose, carboxymethyl cellulose, guar gum or its derivatives, acrylic acid polymers, crosslinked or otherwise, ethylene/maleic anhydride copolymers, methyl vinyl ether/maleic anhydride copolymers, xanthan gum and scleroglucans.

The composition can be thickened by employing the product resulting from the ionic interaction of a cationic polymer consisting of a copolymer of cellulose or of a cellulose derivative grafted with a salt of a watersoluble quaternary ammonium monomer and of a carboxylic anionic polymer which has an absolute capillary viscosity in dimethylformamide or methanol, at a concentration of 5% and at 30° C., which is lower than or equal to $30 \times 10^{-3}$ Pa s, such as described more particularly in French Patent Application No. 2,598,611.

The thickeners which are particularly preferred for thickening or gelling the unrinsed compositions are chosen from acrylic acid polymers, crosslinked or otherwise, and more particularly polyacrylic acids crosslinked with a polyfunctional agent, such as the products sold by Goodrich under the name Carbopol, cellulose derivatives such as indicated above, ethylene/maleic anhydride copolymers such as those sold by Monsanto under the name EMA 91, methyl vinyl ether/maleic anhydride copolymers such as those sold by GAF under the name Gantrez AN (119, 139, 169) and the products resulting from the ionic interaction of polymers such as those described above.

The concentration of thickening agent in these compositions varies between 0.05 and 5%, and preferably between 0.1 and 2%, by weight relative to the total weight of the composition.

The compositions in accordance with the invention may be packaged as an aerosol to be dispensed in spray form and to form lacquers. In this case the composition is employed in the presence of a propellant gas such as, more particularly, carbon dioxide, nitrogen, nitrous oxide, dimethyl ether, volatile hydrocarbons such as butane, isobutane and propane, chlorinated and/or fluorinated hydrocarbons, mixtures of hydrocarbons such as n-butane, isobutane or propane with chlorofluorohydrocarbons. In unrinsed compositions, alkanes, fluoroalkanes, chlorofluoroalkanes and their mixtures are preferably chosen in proportions not exceeding 80% relative to the total weight of the composition.

The cosmetic treatment process making use of the polyorganosiloxanes of formula (I) defined above consists essentially in applying the composition to hair, this application being optionally followed by a rinsing, with a view to improving its gleam, while imparting a light and full appearance to it.

The following examples are intended to illustrate the invention without, however, being limiting in nature.

EXAMPLE 1

A hair gel of the following composition is prepared:

Polysiloxane of formula:

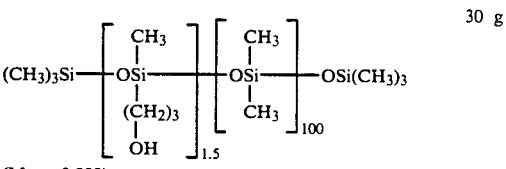

(Mn ≃ 9,000)

30 g

| | |
|---|---|
| Crosslinked polyacrylic acid MW: 4 million, sold by Goodrich under the name Carbopol 940 (neutralized with NH$_4$OH) | 1 g as free acid |
| Triethanolamine q.s. pH | 7 |
| Ethyl alcohol q.s. | 40° |
| Perfume, colorant, preserving agent | |
| Water q.s. | 100 g |

This gel is applied to wet or dry, and preferably dry, hair. The hair gleams and is light.

EXAMPLE 2

A hair aerosol spray of the following composition is prepared:

Polysiloxane of formula:

$$(CH_3)_3Si-\left[\begin{array}{c}CH_3\\|\\OSi\\|\\(CH_2)_3\\|\\OH\end{array}\right]_{2.4}\left[\begin{array}{c}CH_3\\|\\OSi\\|\\CH_3\end{array}\right]_{12.6}-OSi(CH_3)_3 \quad 20\text{ g}$$

(Mn ≃ 1,400)

| | |
|---|---:|
| Perfume q.s. | |
| Ethyl alcohol q.s. | 100 g |
| Aerosol packaging: | |
| Above composition | 30 g |
| 60/40 trichlorofluoromethane/ chlorodifluoromethane | 60 g |
| Ternary mixture of N-butane, >55% isobutane and propane, sold by ELF Aquitaine under the name Aerogaz 3,2 N | 10 g |

EXAMPLE 3

A hairspray of the following composition is prepared:

Polysiloxane of formula:

$$(CH_3)_3Si-\left[\begin{array}{c}CH_3\\|\\OSi\\|\\(CH_2)_3\\|\\OH\end{array}\right]_{2.4}\left[\begin{array}{c}CH_3\\|\\OSi\\|\\CH_3\end{array}\right]_{12.6}-OSi(CH_3)_3 \quad 5\text{ g}$$

(Mn ≃ 1,400)

| | |
|---|---:|
| Perfume, colorant q.s. | |
| Ethyl alcohol q.s. | 100 g |

This spray is packaged in a pump bottle.

EXAMPLE 4

A hairspray of the following composition is prepared:

Polysiloxane of formula:

$$(CH_3)_3Si-\left[\begin{array}{c}CH_3\\|\\OSi\\|\\(CH_2)_3\\|\\OH\end{array}\right]_{4.5}\left[\begin{array}{c}CH_3\\|\\OSi\\|\\CH_3\end{array}\right]_{10.9}-OSi(CH_3)_3 \quad 10\text{ g}$$

(Mn ≃ 1,500)

| | |
|---|---:|
| Perfume q.s. | |
| Ethyl alcohol q.s. | 100 g | which is packaged in a pump bottle.

EXAMPLE 5

A gloss spray of the following composition is prepared:

Polysiloxane of formula:

$$(CH_3)_3Si-\left[\begin{array}{c}CH_3\\|\\OSi\\|\\(CH_2)_3\\|\\OH\end{array}\right]_{1.5}\left[\begin{array}{c}CH_3\\|\\OSi\\|\\CH_3\end{array}\right]_{100}-OSi(CH_3)_3 \quad 1\text{ g}$$

(Mn ≃ 9,000)

| | |
|---|---:|
| Hexamethyldisiloxane sold by Rhone-Poulenc under the name Silbione 70041 V 0.65 q.s. | 100 g |

This composition is packaged in a pump bottle and sprayed onto dry hair.

The hair is light and more gleaming than when treated with a similar composition containing 1% phenylmethylpolysiloxane.

EXAMPLE 6

A conditioner is produced from the following emulsion:

Polysiloxane of formula:

$$(CH_3)_3Si-\left[\begin{array}{c}CH_3\\|\\OSi\\|\\(CH_2)_3\\|\\OH\end{array}\right]_{2.4}\left[\begin{array}{c}CH_3\\|\\OSi\\|\\CH_3\end{array}\right]_{12.6}-OSi(CH_3)_3 \quad 10\text{ g}$$

(Mn ≃ 1,400)

| | |
|---|---:|
| Distearyldimethylammonium chloride | 10 g |
| Preserving agents, perfumes, water, pH 6 q.s. | 100 g |

This cream, applied to washed and roughly dried hair, makes it easier to brush and imparts lightness and sheen to dried hair.

EXAMPLE 7

A conditioner for rinsing, of the following composition, is prepared:

| Polysiloxane of formula: | 5 g |
|---|---:|

$$(CH_3)_3Si-\left[\begin{array}{c}CH_3\\|\\OSi\\|\\(CH_2)_3\\|\\OH\end{array}\right]_{1.5}\left[\begin{array}{c}CH_3\\|\\OSi\\|\\CH_3\end{array}\right]_{100}-OSi(CH_3)_3$$

(Mn ≃ 9,000)

| | |
|---|---:|
| Carbopol 934 (Goodrich) | 0.5 g |
| Glucoside alkyl ether of structure: | 3 g AS |

[Structure: glucoside alkyl ether with CH$_2$OH, OH groups and terminal O—R, subscript n]

(R = linear C$_8$–C$_{10}$ alkyl)
(n = 0, 1, 2 etc.)
sold at a concentration of 302 AS by

| -continued | |
|---|---|
| Seppic under the name Triton CG 110 | |
| Stearyl alcohol | 1 g |
| Cetyl alcohol | 1 g |
| Triethanolamine pH = 5.5 q.s. | |
| Perfume, preserving agents, water q.s. | 100 g |

This conditioner is applied to washed and roughly dried hair. After a few minutes' interval it is rinsed off.

The wet hair is easily untangled and is smooth.

The dried hair is soft, tangle-free and gleaming.

We claim:

1. Cosmetic hair-care composition, which contains, in a cosmetically acceptable medium, a polyorganosiloxane containing a hydroxyalkyl functional group corresponding to the following formula (I):

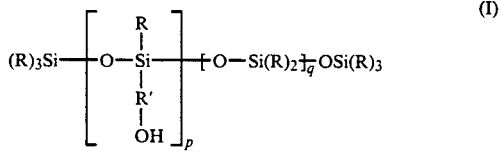

in which the radicals R, which are identical or different, are chosen from methyl and phenyl radicals, at least 60 mol % of the radicals R being methyl radicals, the radical R' is a linear or branched divalent alkylene hydrocarbon chain containing from 2 to 18 carbon atoms, p is an integer between 1 and 30 inclusive, q is an integer between 1 and 120 inclusive, in sufficient proportions to impart to the hair good sheen properties combined with a light and full appearance, said composition containing no anionic surfactant in concentrations more than 5% by weight based on the total weight of the composition which confer foaming properties to the composition.

2. Composition according to claim 1, wherein in the compounds of formula (I) R' denotes a linear or branched divalent alkylene hydrocarbon chain containing from 2 to 6 carbon atoms.

3. Composition according to claim 1, wherein in the compounds of formula (I) R' is the trimethylene radical: —(CH$_2$—$)_3$ or a 2-methyltrimethylene chain:

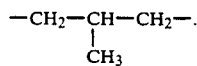

4. Composition according to claim 1, which contains, in a cosmetically acceptable medium, a polyorganosiloxane containing a hydroxyalkyl functional group of formula (I) in concentrations of between 0.5% and 50% by weight relative to the total weight of the composition.

5. Composition according to claim 1, which is in the form of an aqueous, alcoholic or hydroalcoholic lotion, thickened or otherwise, in the form of a gel, or packaged as an aerosol or in a pump bottle to form a spray.

6. Composition according to claim 1, which additionally contains at least one or more adjuvants which are usually employed in cosmetics, selected from the group consisting of perfumes, colorants, preserving agents, nonionic, cationic or amphoteric surfactants or a mixture thereof, thickeners, sunscreens and active substances.

7. Composition according to claim 1, which is in the form of a lotion containing from 50 to 99.5% by weight, and preferably from 70 to 98% by weight, relative to the total weight of the composition, of a solvent selected from the group consisting of lower $C_2$-$C_4$ alkanols, volatile silicones or hydrocarbons chosen from butane and chlorofluorohydrocarbons or mixtures thereof.

8. Composition according to claim 1, which is thickened or gelled with an agent selected from the group consisting of cellulose derivatives, guar gum and its derivatives, acrylic acid polymers, crosslinked or otherwise, ethylene/maleic anhydride copolymers, methyl vinyl ether/maleic anhydride copolymers, xanthan gum, scleroglucans, the product of the ionic interaction between a cationic polymer consisting of a copolymer of cellulose or a cellulose derivative grafted with a salt of a water-soluble quaternary ammonium monomer and a carboxylic anionic polymer which has an absolute capillary viscosity in dimethylformamide or methanol, at a concentration of 5% and at 30° C., which is lower than or equal to $30 \times 10^{-3}$ Pa s, this thickening agent is present in proportions of between 0.05 and 5% and preferably between 0.1 and 2% by weight relative to the total weight of the composition, the solvent medium consisting of water or a water/$C_2$-$C_4$ alcohol mixture, the quantity of alcohol being between 0 and 50%.

9. Composition according to claim 1, which is packaged as an aerosol in the presence of a propellent gas, to form a spray at the time of expulsion.

10. Composition according to claim 1 which is in the form of an unrinsed gel, lotion or lacquer for hair-setting or blow drying.

11. Cosmetic hair-care composition comprising, in a cosmetically acceptable medium, a polyorganosiloxane containing a hydroxyalkyl functional group corresponding to the formula (I)

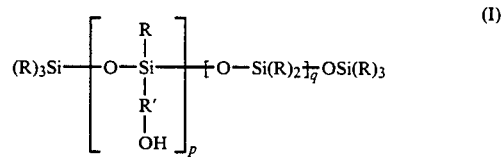

in which the radicals R, which are identical or different, are chosen from methyl and phenyl radicals, at least 60 mol % of the radicals R being methyl radicals, the radical R' is a linear or branched divalent alkylene hydrocarbon chain containing from 2 to 18 carbon atoms, p is an integer between 1 and 30 inclusive, q is an integer between 1 and 120 inclusive, in concentrations between 0.5 and 50% by weight based on the total weight of the composition, said composition containing no anionic surfactant in concentrations more than 5% by weight based on the total weight of the composition which confer foaming properties thereto.

12. Composition according to claim 1 which contains in a cosmetically acceptable medium, a polyorganosiloxane containing a hydroxyalkyl functional group of formula (I) in concentration of between 1 and 30% by weight relative to the total weight of the composition.

13. Process for a cosmetic treatment of hair, which consists in applying to the hair at least one composition such as defined in claim 1 without this application being followed by a rinsing.

14. Process for a cosmetic treatment of hair, which consists in applying to the hair a composition such as defined in claim 1, this application being followed by a rinsing.

* * * * *